(12) United States Patent
Qu et al.

(10) Patent No.: US 10,288,674 B2
(45) Date of Patent: May 14, 2019

(54) IMPEDANCE CHARACTERISTIC CIRCUIT FOR ELECTROCHEMICAL SENSOR

(71) Applicant: Analog Devices Global, Hamilton (BM)

(72) Inventors: GuangYang Qu, Beijing (CN); Junbiao Ding, Beijing (CN); Tony Yincai Liu, Beijing (CN); Shurong Gu, Beijing (CN); Yimiao Zhao, Beijing (CN); Hanqing Wang, Beijing (CN); Leicheng Chen, Rongjiang Town (CN)

(73) Assignee: Analog Devices Global, Hamilton (BM)

( * ) Notice: Subject to any disclaimer, the term of this patent is extended or adjusted under 35 U.S.C. 154(b) by 177 days.

(21) Appl. No.: 15/586,869

(22) Filed: May 4, 2017

(65) Prior Publication Data
US 2018/0321302 A1 Nov. 8, 2018

(51) Int. Cl.
*G01R 31/28* (2006.01)
*G01R 15/16* (2006.01)
(Continued)

(52) U.S. Cl.
CPC ......... *G01R 31/2829* (2013.01); *G01R 15/16* (2013.01); *G01N 27/416* (2013.01);
(Continued)

(58) Field of Classification Search
CPC ...... G01R 31/00; G01R 31/28; G01R 31/282; G01R 31/2829; G01R 19/00;
(Continued)

(56) References Cited

U.S. PATENT DOCUMENTS 4,638,260 A * 1/1987 Hamley ............... H03F 1/34
330/254
4,916,641 A * 4/1990 Bybee ............... F15B 19/00
702/83
(Continued)

FOREIGN PATENT DOCUMENTS

EP 1262755 A1 12/2002

OTHER PUBLICATIONS

"Analog Devices ADuDM350 Hardware Reference Manual UG-587", Rev. C, © 2014-2016, (2014-2016), 459 pgs.
(Continued)

*Primary Examiner* — Hoai-An D. Nguyen
(74) *Attorney, Agent, or Firm* — Schwegman Lundberg & Woessner, P.A.

(57) ABSTRACT

A electrochemical or other sensor interface circuit architecture can deliver substantial DC offset bias to an electrochemical or other sensor separately or independently from delivering a time-varying AC excitation signal, which can then be provided with higher resolution, which, in turn, can allow better resolution of the measured response signal providing the impedance characteristic of sensor condition. For example, a differential time-varying AC excitation signal for the sensor condition characteristic can be delivered separately and independently from a differential stable (e.g., DC or other) bias signal, such as by using separate digital-to-analog converters (DACs), so that providing the more stable signal does not limit the resolution and accuracy of the time-varying signal, such as by using up the dynamic range of a single DAC.

21 Claims, 4 Drawing Sheets

(51) Int. Cl.
  *G01R 27/02* (2006.01)
  *G01N 27/417* (2006.01)
  *G01N 27/416* (2006.01)

(52) U.S. Cl.
  CPC ..... *G01N 27/4163* (2013.01); *G01N 27/4175* (2013.01); *G01R 27/02* (2013.01)

(58) Field of Classification Search
  CPC .... G01R 19/2506; G01R 15/00; G01R 15/14; G01R 15/16; G01R 27/00; G01R 27/02; G01R 27/26; G01R 27/2617; G01R 27/2635; G01N 27/00; G01N 27/26; G01N 27/416; G01N 27/4163; G01N 27/4175; G01N 33/00; G01N 33/0006; G01N 33/007; G01N 35/00; G01N 35/00623; G01N 35/00693
  USPC .................. 324/600, 602, 603, 76.11, 76.12; 204/193, 194, 400, 401; 702/108, 116, 702/117
  See application file for complete search history.

(56) References Cited

U.S. PATENT DOCUMENTS

| | | | |
|---|---|---|---|
| 4,968,946 A | | 11/1990 | Maier |
| 5,004,986 A | * | 4/1991 | Bohrer ................... G05F 3/265 323/313 |
| 5,440,219 A | * | 8/1995 | Wilkerson ................ H02P 1/42 318/459 |
| 6,452,405 B1 | | 9/2002 | Collier-Hallman |
| 2005/0110103 A1 | * | 5/2005 | Setlak ................... G06K 9/0002 257/414 |
| 2006/0263254 A1 | | 11/2006 | Lee |
| 2012/0065540 A1 | | 3/2012 | Yarden et al. |
| 2012/0078071 A1 | * | 3/2012 | Bohm ................ A61B 5/14532 600/345 |
| 2013/0085439 A1 | * | 4/2013 | Sansoucy ............ A61M 1/3655 604/9 |
| 2013/0102061 A1 | | 4/2013 | Coursey et al. |
| 2017/0067844 A1 | * | 3/2017 | Vellaisamy .......... G01N 27/414 |
| 2018/0321186 A1 | | 11/2018 | Looney et al. |

OTHER PUBLICATIONS

"Analog Devices 16-Bit Precision, Low Power Metter on a Chip with Cortex-M3 and Connectivity", © 2014 Analogy Devices, Inc., Data Sheet ADuCM350 Rev. A, (2014), 41 pgs.

"Designing a PotentioStatic Cicuit", Alphasense Application Note— AAN 105-03, (Mar. 2009), 5 pgs.

U.S. Appl. No. 15/586,848, filed May 4, 2017, Multiple String, Multiple Output Digital to Analog Converter.

U.S. Appl. No. 15/586,849, filed May 4, 2017, Systems and Methods for Determining the Condition of a Gas Sensor.

U.S. Appl. No. 15/586,877, filed May 4, 2017, Internal Integrated Circuit Resistance Calibration.

* cited by examiner

IMPEDANCE CHARACTERISTIC CIRCUIT FOR ELECTROCHEMICAL SENSOR

CROSS-REFERENCE TO RELATED PATENT DOCUMENTS

This patent application is also related to: (1) a U.S. Patent Application, filed on May 4, 2017, entitled MULTIPLE STRING, MULTIPLE OUTPUT DIGITAL TO ANALOG CONVERTER (U.S. patent application Ser. No. 15/586,848), naming Shurong Gu, Dennis A. Dempsey, GuangYang Qu, Hanqing Wang, and Tony Yincai Liu as inventors, the disclosure of which is hereby incorporated herein by reference, in its entirety, including its disclosure of a dual-output DAC; (2) a U.S. Patent Application, filed on May 4, 2017, entitled INTERNAL INTEGRATED CIRCUIT RESISTANCE CALIBRATION (U.S. patent application Ser. No. 15/586,877), naming GuangYang Qu, Leicheng Chen, and Michael Looney as inventors, the disclosure of which is hereby incorporated herein by reference, in its entirety, including its disclosure of resistance measurement or calibration; and (3) a U.S. Patent Application, filed on May 4, 2017, entitled SYSTEMS AND METHODS FOR DETERMINING THE CONDITION OF A GAS SENSOR (U.S. patent application Ser. No. 15/586,849), naming Michael Looney and GuangYang Qu as inventors, the disclosure of which is hereby incorporated herein by reference, in its entirety, including its disclosure of impedance measurement systems and methods.

TECHNICAL FIELD

This document pertains generally, but not by way of limitation, to electrochemical sensors and circuits, and more particularly but not by way of limitation, to a sensor interface circuit for determining a sensor characteristic such as impedance.

BACKGROUND

An electrochemical sensor can be used for various applications, such as for sensing the presence of one or more constituent gases, such as oxygen, carbon monoxide, etc., in an environment around the electrochemical sensor. The electrochemical sensor can include a counter electrode (CE), a reference electrode (RE), and a sensing electrode (SE). The sensing electrode can also be referred to as a working electrode (WE). The electrochemical sensor can include one or more sensor characteristics, such as impedance, which can provide an indication of how effectively the sensor is still operating, such as by comparing a sensor characteristic to a specified reference value. This can help determine whether or when to replace a failing electrochemical sensor, or to determine how much useful life can be expected from the electrochemical sensor before replacement.

SUMMARY

Determining a sensor condition characteristic can involve impedance testing of the sensor. The present inventors have recognized, among other things, that such impedance testing may involve providing a time-varying AC excitation current signal into the sensor and measuring a response voltage, which can provide a sensor condition characteristic by indicating an impedance of the electrochemical sensor. The present inventors have recognized that one problem to be solved is providing both a substantial DC bias voltage to the electrochemical sensor and an accurate, high-resolution excitation current signal to the sensor. For example, if a single digital-to-analog converter (DAC) is used to generate both the DC bias voltage to the electrochemical sensor and the time-varying AC excitation signal for testing the impedance of the sensor, the resolution of the time-varying excitation signal may be constrained by the available dynamic range of the DAC, because providing the DC offset bias voltage can use up a significant portion of the dynamic range of the DAC. Accordingly, the present inventors have solved this problem by providing a sensor interface circuit architecture that is capable of delivering a substantial DC offset bias to an electrochemical or other sensor separately or independently from delivering a time-varying AC excitation signal, which can then be provided with higher resolution, which, in turn, can allow better resolution of the measured response signal providing the impedance characteristic of sensor condition. A better indication of sensor condition can help avoid premature replacement of the electrochemical sensor, can help avoid leaving a failed sensor in place, or both. This can be important, for example, for an electrochemical sensor in an application to detect and alert for a dangerous level of carbon monoxide, as well as for other electrochemical sensor applications. This can also be useful for other impedance sensing applications, or other sensor characteristic determination applications.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

This document describes, among other things, a sensor condition characteristic interface circuit architecture that is capable of delivering a substantial DC offset bias to an electrochemical or other sensor separately or independently from delivering a time-varying AC excitation signal, which can then be provided with higher resolution, which, in turn, can allow better resolution of the measured response signal providing the impedance characteristic of sensor condition. A better indication of sensor condition can help avoid premature replacement of the electrochemical sensor, can help avoid leaving a failed sensor in place, or both. This can be important, for example, for an electrochemical sensor in an application to detect and alert for a dangerous level of carbon monoxide, as well as for other electrochemical sensor applications. This can also be useful for other impedance sensing applications, or other sensor condition characteristic testing applications.

Figure 1:
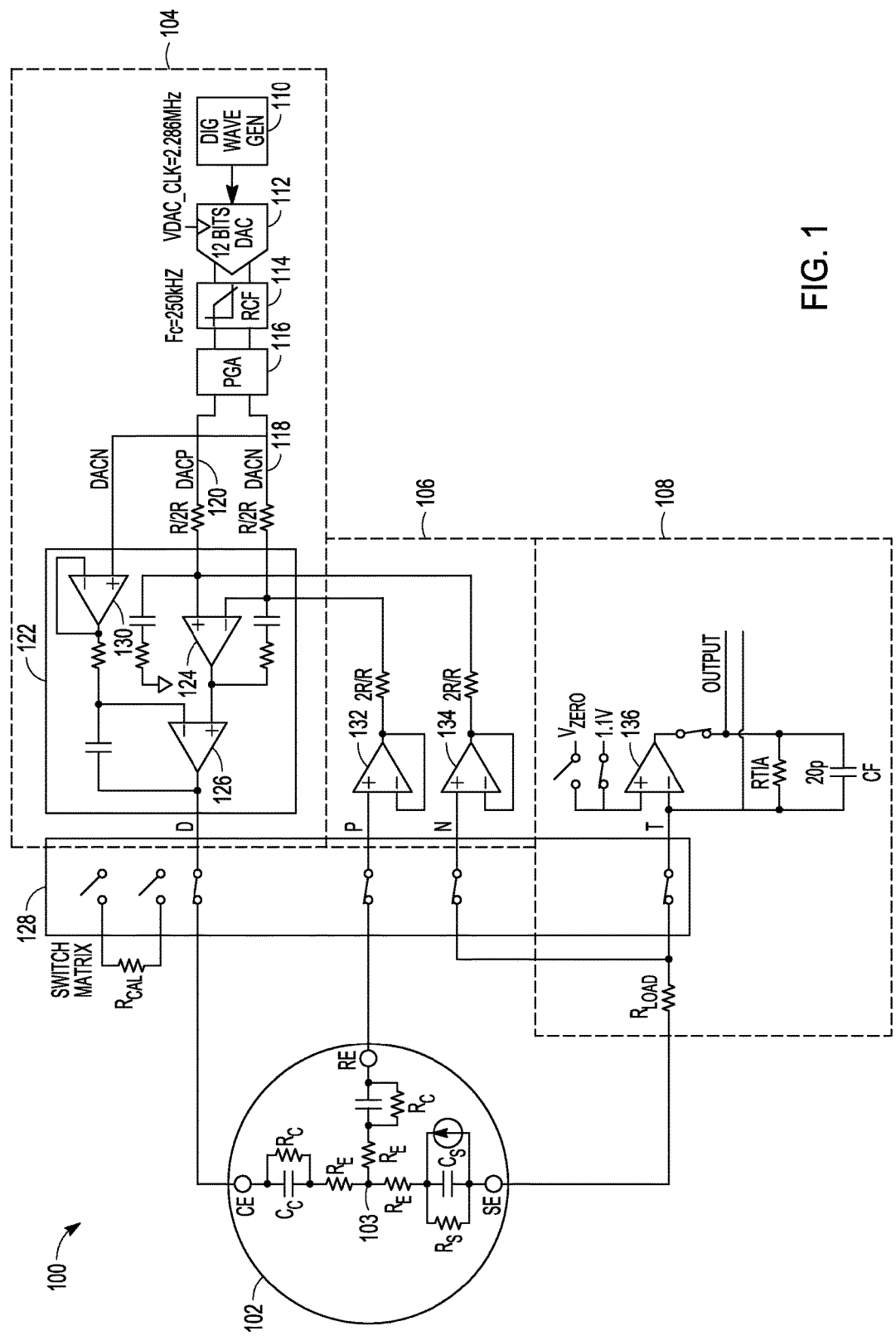
FIG. 1 shows an example of a first approach to providing a sensor condition characteristic interface circuit to an electrochemical sensor that senses a gas or a constituent component of a gas.

FIG. 1 shows an example of a first approach to providing a sensor characteristic indication interface circuit 100 to an electrochemical sensor 102 that senses a gas or a constituent component of a gas. The electrochemical sensor 102 can include a counter electrode (CE) terminal, a reference electrode (RE) terminal, and a sensing electrode (SE) terminal. The sensor characteristic interface circuit 100 can include a sensor condition indication capability, such as for performing an impedance test of the sensor 102. In FIG. 1, the electrochemical sensor 102 is represented by an electrical model of characteristic impedances associated with the various electrodes, which can include resistive components and reactive (e.g., capacitive) components as shown. Each electrode can be modeled as a series resistance in series with a parallel combination of a resistance and capacitance, electrically connected at a common node 103.

In FIG. 1, the sensor characteristic interface circuit 100 can include a sensor excitation circuit 104, a feedback circuit 106, and a response signal output circuit 108. The sensor excitation circuit 104 can include a digital waveform generator circuit 110, such as for generating a digital excitation signal for further processing and delivery to the sensor 102, for generating a bias signal for further processing and delivery to the sensor 102, or both. One or more outputs of the digital waveform generator 110 can be coupled to inputs of a digital-to-analog converter (DAC) circuit 112, for example, a 12-bit DAC. The DAC 112 can convert the digital excitation signal waveform provided by the digital waveform generator 110 to an analog signal, such as a differential mode analog signal, which can be provided at one or more outputs of the DAC 112. This resulting analog signal can be filtered, such as by providing the DAC output signal to one or more inputs of an active or passive single pole or multiple pole lowpass filter circuit 114, for example, a single-pole lowpass filter having a cutoff frequency of Fc=250 kHz. The resulting filtered analog signal can be provided at one or more outputs of the filter circuit 114 to one or more inputs of an amplification or attenuation circuit, such as a programmable gain amplifier (PGA) circuit 116. In an example, the PGA 116 can provide attenuation (gain of less than 1) so that more full dynamic range and resolution of the DAC 112 can be utilized.

In FIG. 1, the resulting filtered and amplified or attenuated analog signal can be provided at one or more outputs of the PGA 116 to differential inputs 118, 120 of an excitation amplifier circuit 122, which itself can include a differential input first amplifier circuit 124 having an inverting input and a non-inverting input. For example, the PGA output 118 can be coupled to the inverting input of the amplifier 124, such as via a first resistor (which can optionally include an R/2R programmable resistance resistor ladder configuration), and the PGA output 120 can be coupled to the non-inverting input of the amplifier 124, such as via a second resistor (which can also optionally include an R/2R programmable resistance resistor ladder configuration). The amplifier 124 can be used to drive a further second amplifier 126, which can provide the excitation signal at an output of the excitation amplifier circuit 122 at node D to an electrode of the sensor 102, such as to the counter electrode CE via a switch that can be included as part of a switch matrix 128, which can be included on the same integrated circuit as the rest of the sensor interface circuit 100. Within the excitation amplifier circuit 122, a third amplifier circuit 130 can be used, for example, in a voltage-follower configuration, to provide a bias voltage to the inverting input of the second amplifier 126.

In FIG. 1, the feedback circuit 106 can include a first input (P) that can be electrically coupled to one of the electrodes of the sensor 102, such as to the reference electrode (RE) terminal, such as via a corresponding switch in the switch matrix 128. The feedback circuit 106 can also include a second input (N) that can be electrically coupled to one of the electrodes of the sensor 102, such as to the sensing electrode (SE) terminal, such as via another corresponding switch in the switch matrix 128, and optionally via a load resistor ($R_{LOAD}$). The P and N inputs of the feedback circuit 106 can be respectively coupled to and received by corresponding first and second buffer amplifier circuits 132, 134, each of which can be configured in a voltage-follower configuration with a non-inverting input of the buffer amplifier circuit 132, 134 electrically coupled to the corresponding output of the buffer amplifier circuit 132, 134. The output of the buffer amplifier circuit 132 can be electrically coupled to the inverting input of the first amplifier circuit 124, such as via a corresponding resistor (which can optionally include an R/2R programmable resistance resistor ladder configuration). The output of the buffer amplifier circuit 134 can be electrically coupled to the non-inverting input of the first amplifier circuit 124, such as via a corresponding resistor (which can optionally include an R/2R programmable resistance resistor ladder configuration).

In FIG. 1, the sensing electrode (SE) terminal can be connected to the response signal output circuit 108, such as to a transimpedance amplifier node (T) via a corresponding switch in the switch matrix 128. The response signal output circuit 108 can include a transimpedance amplifier 136 to convert a current received from the sensing electrode (SE) terminal of the sensor 102 (e.g., via the load resistor $R_{LOAD}$, or otherwise) in to a response voltage signal provided at the output node of the transimpedance amplifier 136. The transimpedance amplifier 136 can be configured with a feedback resistor, $R_{TIA}$, in a feedback path between the output of the transimpedance amplifier 136 and an inverting input, at node T, of the transimpedance amplifier 136. A feedback capacitor (CF) can optionally be placed in parallel with the feedback resistor, $R_{TIA}$, such as to provide lowpass filtering of the response voltage signal at the output of the transimpedance amplifier 136, if desired.

In FIG. 1, the excitation amplifier circuit 122 can include a differential input first amplifier 124 having its differential inputs (non-inverting input and inverting input), respectively coupled to receive and sum currents from two differential sources: first, from the respective outputs of the PGA 116, via their corresponding resistors, and second, from the respective outputs of the buffer amplifier circuits 132, 134, via their corresponding resistors.

During an impedance testing mode of operation, the digital waveform generator circuit 110 can superimpose a time-varying AC signal component upon a stable DC bias signal voltage component desired for operating the sensor 102. In response to this time-varying AC signal component in this impedance testing mode of operation, a resulting time-varying AC signal voltage, will appear in response at the output of the TIA amplifier 136, from which a characteristic impedance parameter of the sensor 102 can be determined (e.g., by dividing the AC response signal voltage component amplitude by the AC excitation current signal component).

One issue with the approach shown in FIG. 1 is providing both a substantial DC bias voltage to the electrochemical sensor 102 together with an accurate, high-resolution time-varying AC excitation current signal to the sensor 102. In the approach shown in FIG. 1, a single DAC 112 is used to generate both the DC bias voltage to the electrochemical sensor 102 and the time-varying AC excitation signal for testing the impedance of the sensor 102. Because of this, the resolution of the time-varying AC excitation signal may be constrained by the available dynamic range of the DAC 112. This is because providing the DC offset bias voltage can use up a significant portion of the dynamic range of the DAC 112.

Figure 2:
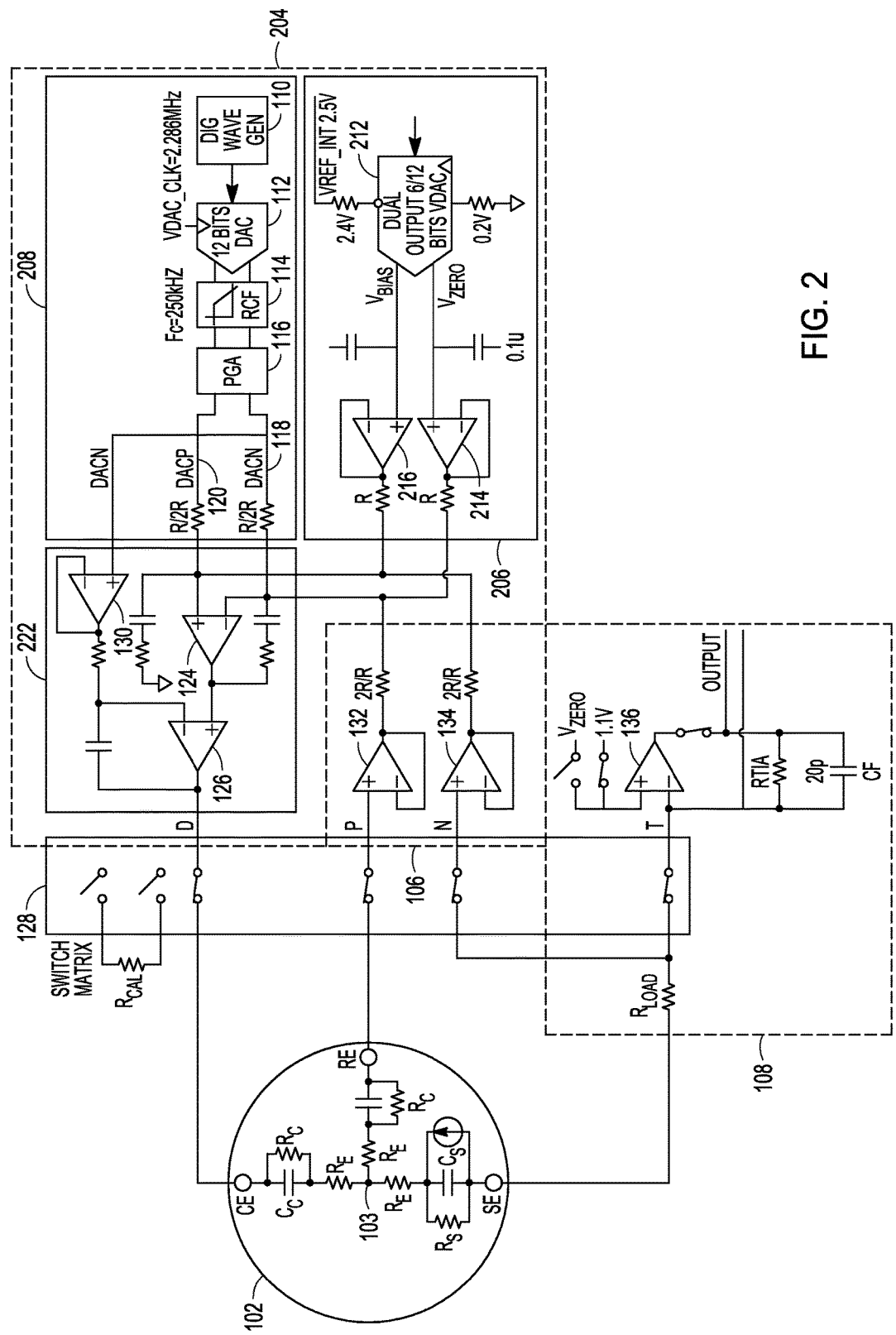
FIG. 2 shows an example of a second approach to providing a sensor characteristic condition interface circuit to an electrochemical sensor, similar to that shown in FIG. 1, but in which the sensor excitation circuit can be replaced by a sensor excitation circuit that can include a differential stable bias circuit that can be separate and independent from a time-varying AC excitation signal generator circuit.

FIG. 2 shows an example of a second approach to providing a sensor characteristic interface circuit 200 to an electrochemical sensor 102, similar to that shown in FIG. 1, but in which the sensor excitation circuit 104 can be replaced by a sensor excitation circuit 204 that can include a differential stable bias circuit 206 that can be separate and independent from a time-varying AC excitation signal generator circuit 208. The differential stable bias circuit 206 can provide a stable differential bias signal component to the shared excitation amplifier circuit 222, which is similar in certain respects to the excitation amplifier 122, but which can include an additional set of inputs that can be coupled to the differential stable bias circuit 106. The time-varying AC excitation signal generator circuit 208 can provide a time-varying AC excitation signal component to the shared excitation amplifier circuit 222, but without being required to also provide a differential stable bias signal to the shared excitation amplifier circuit 222. This can help enable improved resolution of the time-varying AC signal component provided to the shared excitation amplifier circuit 222, since the full dynamic range of the DAC 112 can be used to generate the time-varying AC signal component, without also requiring the dynamic range of the DAC 112 to accommodate the differential stable bias signal. The shared excitation amplifier circuit 222 can include a third pair of differential inputs that can be coupled to the feedback circuit 106, in addition to a first set of differential inputs that can be coupled to the time-varying AC excitation signal generator circuit 208, and a second set of differential inputs that can be coupled to the differential stable bias signal generator circuit 206. The third pair of differential inputs can be used to provide the differential stable bias signal to the amplifier circuit 222 separately and independently from the time-varying AC excitation signal and the feedback signal.

In FIG. 2, the differential stable bias signal generator circuit 206 can include a second DAC 212, which can be separate from and be operate independently from the DAC 112 of the time-varying AC excitation signal generator circuit 208, such as to separately provide the differential stable bias signal component to the shared excitation amplifier circuit 222, thereby helping free up the dynamic range of the DAC 112, such as to provide a higher resolution time-varying AC signal component to the shared excitation amplifier circuit 222. The second DAC 212 need not have the same resolution as the DAC 112. For example, the second DAC 212 may have a lower resolution than the DAC 112, because a lower resolution may be suitable for providing the differential stable bias signal component to the shared excitation amplifier circuit 222. As an illustrative example, the second DAC 212 may have a 6-bit resolution and receive a 6-bit digital input signal, while the first DAC 112 may have a 12-bit resolution and may receive a 12-bit digital input signal. However, the DAC 212 can have the same resolution as the DAC 112, or the DAC can have a greater resolution than the DAC 112, if desired, as appropriate for a particular application. In an example, the DAC 112 can include a dual-output DAC providing a first output, at node Vbias, at a higher resolution (e.g., 12 bits resolution) than that provided by the dual-output DAC at its second output (e.g., 6 bits resolution), at node Vzero. In an example, the dual-output DAC 112 can be implemented such as described in a U.S. Patent Application, filed May 4, 2017, entitled MULTIPLE STRING, MULTIPLE OUTPUT DIGITAL TO ANALOG CONVERTER (U.S. patent application Ser. No. 15/586,848), naming Shurong Gu, Dennis A. Dempsey, GuangYang Qu, Hanging Wang, and Tony Yincai Liu as inventors, the disclosure of which is hereby incorporated herein by reference, in its entirety, including its disclosure of a dual-output DAC.

In FIG. 2, the DAC 212 can provide its stable bias signal component at differential outputs, which can be further stabilized by optional respective shunt capacitors (e.g., 0.1 microFarad) respectively coupled to such differential outputs of the DAC 212. Signals from these differential outputs of the DAC 212 can be received at inputs of buffer amplifier circuits 214, 216, such as at respective non-inverting inputs of the respective buffer amplifier circuits 214, 216. The buffer amplifier circuits 214, 216 can each be configured in a voltage-follower configuration with its inverting input terminal coupled in a feedback arrangement to its output terminal. The output of the buffer amplifier circuit 214 can be coupled to an inverting input of the amplifier 124 in the shared excitation amplifier circuit 222, such as via a resistor having a resistance value R. The output of the buffer amplifier 216 can be coupled to a non-inverting input of the amplifier 124, such as via a resistor having a resistance value R.

Thus, in FIG. 2, the shared excitation amplifier 222 can include three pairs of differential inputs: (1) a first pair of differential inputs from the differential time-varying AC excitation signal generator circuit 208, such as to receive a differential time-varying AC excitation signal component, such as for application to the sensor 102 during impedance testing; (2) a second pair of differential inputs from the differential stable bias signal generator 206, such as to receive a differential stable bias signal component, such as for application to the sensor 102 during impedance testing, or during normal gas-sensing operation; and (3) a third pair of differential inputs from the feedback circuit 106, such as to receive a differential feedback signal from the sensor 102, such as during impedance testing, or during normal gas-sensing operation. Individual ones of these three pairs of differential inputs can be respectively coupled to the non-inverting and inverting inputs of the amplifier 124 of the shared excitation amplifier 222, such as via corresponding fixed or variable resistors, or otherwise.

In FIG. 2, separately and independently providing the differential time-varying AC signal component from the differential stable bias signal component can allow the DAC 112 providing the differential time-varying AC signal component to provide a more accurate, higher resolution differential time-varying AC signal, because its dynamic range can be used more fully, since it need only accommodate the amplitude of the differential time-varying AC signal, instead of that AC amplitude superimposed upon the signal offset of the differential stable bias signal component. The superpositioning of the differential time-varying AC signal component is performed by the shared excitation amplifier circuit 222, which can leave the dynamic ranges of each of the DACs 112, 212 unconstrained by the signal provided to the other of the DACs 112, 212.

The differential stable bias signal component can be a dc component, which does not vary over time, in an example, or it can be "stable" in the sense that the differential stable bias signal component is time-varying, but with a frequency is less than that of the differential time-varying AC signal, such as 2×, 5×, 10×, 100×, 1000×, 1,000,000×, less than the frequency of the differential time-varying AC signal.

Although FIG. 2 shows an example in which the DAC 112 and the DAC 212 are completely separate and independent, the reason for providing such an arrangement can be so that their two different input signals can be independently provided to permit full use of the entire dynamic range of each of the DACs 112, 212. The present inventors contemplate and envision that it may be possible to share certain components of the DACs 112, 212, while still allowing each of two digital input signals to be separately and independently provided, each without imposing any dynamic range constraint on the other, even though certain components may be shared between the DACs 112, 212.

Figure 3:
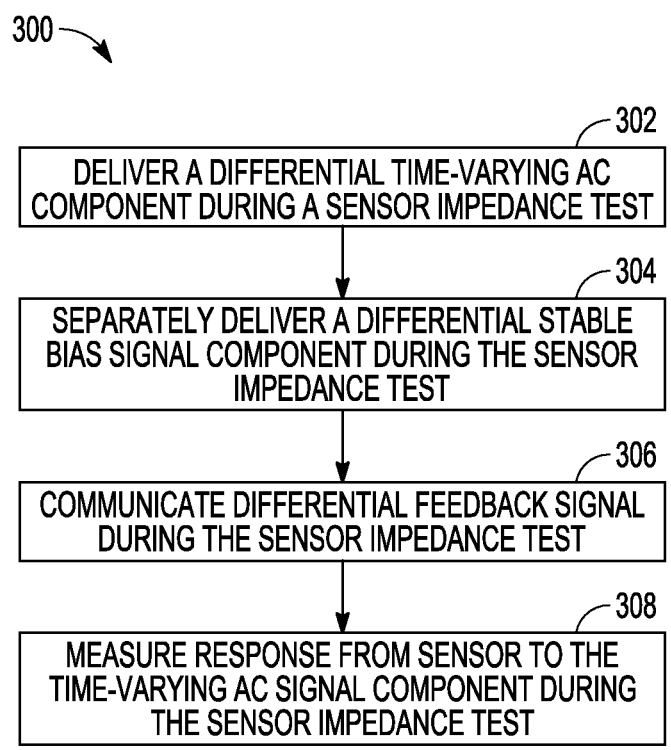
FIG. 3 shows an example of portions of a method, such as for determining usability of an electrochemical sensor, such as by determining a sensor characteristic.

FIG. 3 shows an example of portions of a method 300, such as for determining usability of an electrochemical sensor, such as by determining a sensor characteristic, such as an impedance, associated with the electrochemical sensor, such as the electrochemical sensor 102.

At 302, a differential time-varying AC excitation signal component can be delivered, such as to first and second amplifier input nodes (e.g., the non-inverting and inverting inputs of the amplifier 124 of the shared excitation amplifier circuit 222), such for driving an excitation signal into the sensor 102 during a sensor impedance test.

At 304, a differential stable bias signal component can be separately (and concurrently) delivered, such as to the first and second amplifier input nodes (e.g., the non-inverting and inverting inputs of the amplifier 124 of the shared excitation amplifier circuit 222), such as for biasing the first and second amplifier input nodes while driving the excitation signal into the sensor 102 during the sensor impedance test. This can be useful for providing a desired bias signal to the sensor 102, such as may be needed for operating the sensor 102.

At 306, a differential feedback signal can be communicated (e.g., concurrently to 302 and 304 during the sensor impedance test) from the sensor 102, such as to the first and second amplifier input nodes, while driving the excitation signal into the sensor 102.

At 308, a response from the sensor can be measured while driving the excitation signal into the sensor 102 during the sensor impedance test, such as using the transimpedance amplifier 136 of the response signal output circuit 108. A response voltage at the output of the transimpedance amplifier 136 can provide an indication of the impedance of the sensor 102, such as when the current being provided to the sensor 102 (e.g., determined by the differential time-varying AC input is known). Thus, although the impedance of the sensor 102 is being determined, such impedance can be determined by measuring a response voltage to a specified amplitude AC excitation signal current, using Ohm's law, which states that the impedance is equal to the response voltage divided by the specified sensor current.

In FIG. 3, at 302, delivering the time-varying AC excitation signal can include converting a first digital input signal into a first analog signal for providing the differential time-varying AC excitation signal component during the sensor impedance test. At 304, delivering the differential stable bias signal component can include converting a second digital input signal into a second analog signal for providing the differential stable bias signal component during the sensor impedance test. The second analog signal can also optionally be used for providing the differential stable bias signal component during an operating (e.g., gas-sensing) mode of the sensor during which the differential time-varying AC signal component is not applied, e.g., sensor impedance is not being tested.

In FIG. 3, at 302, providing the differential time-varying AC excitation signal component during the sensor impedance test can optionally include attenuating the first analog signal, such as using PGA 116. This can help make use of the full dynamic range of the DAC 112 for providing a high resolution signal for the AC excitation for impedance testing of the sensor 102.

In FIG. 3, at 308, measuring the response from the sensor 102 can optionally include converting a current from the sensor 102 in response to the differential time-varying AC excitation signal component into a voltage (e.g., at the output of the transimpedance amplifier 136) to provide an indication of a sensor characteristic (e.g., impedance) related to usability of the sensor 102. In an illustrative example, the current from the sensor 102 can optionally be provided by coupling through the load resistor, $R_{LOAD}$. However, including the load resistor, $R_{LOAD}$, is not required. In an example, the transimpedance amplifier 136 can optionally be operated with a direct connection to the sensor 102, e.g., omitting the load resistor, $R_{LOAD}$.

In FIG. 3, at 302, the frequency of the differential time-varying AC signal component can optionally be varied during the sensor impedance test. This can include performing the impedance test at two different frequencies. In an example, both frequencies of the impedance test signal can be higher than a frequency response of the sensor 102 expected to even a rapid change in environmental conditions, such as can include a change in concentration of the gas being tested, a change in environmental temperature at which the sensor 102 is being operated, etc., such that these factors can be reduced or eliminated using a differential impedance test at different frequencies. In an example, performing the impedance test can include providing a wide sweep of the frequency (e.g., from 0.2 Hz to 200 kHz) of the differential time-varying AC signal component, and measuring the response signal during two or more points of the sweep.

In FIG. 3, at 304, providing the differential stable bias signal component can include temperature compensating the differential stable bias signal component, such as by providing at least one of a proportional-to-absolute-temperature (PTAT) or complementary-to-absolute-temperature (CTAT) signal to generate the differential stable bias signal component.

Although FIG. 2 shows an example having three differential inputs (e.g., a first differential input pair to receive a differential time-varying AC excitation signal component, a second differential input pair to receive a differential stable bias signal component, and a third differential input pair to receive a differential feedback signal component), a fourth or even further differential inputs can also be included to similarly input or otherwise couple or more corresponding further differential signal components.

Also, although the electrochemical sensor 102 is shown as having three electrodes (RE, CE, SE), a fourth or even further electrodes can be included in the electrochemical sensor 102. For example, a fourth diagnostic electrode (DE) can be included in the electrochemical sensor 102, and the nodes N and T shown in FIG. 2 can be alternatively or selectively (e.g., switchably) coupled to the diagnostic electrode (DE), e.g., instead of (or as a switchable alternative to) being coupled to the sensing electrode (SE).

Figure 4:
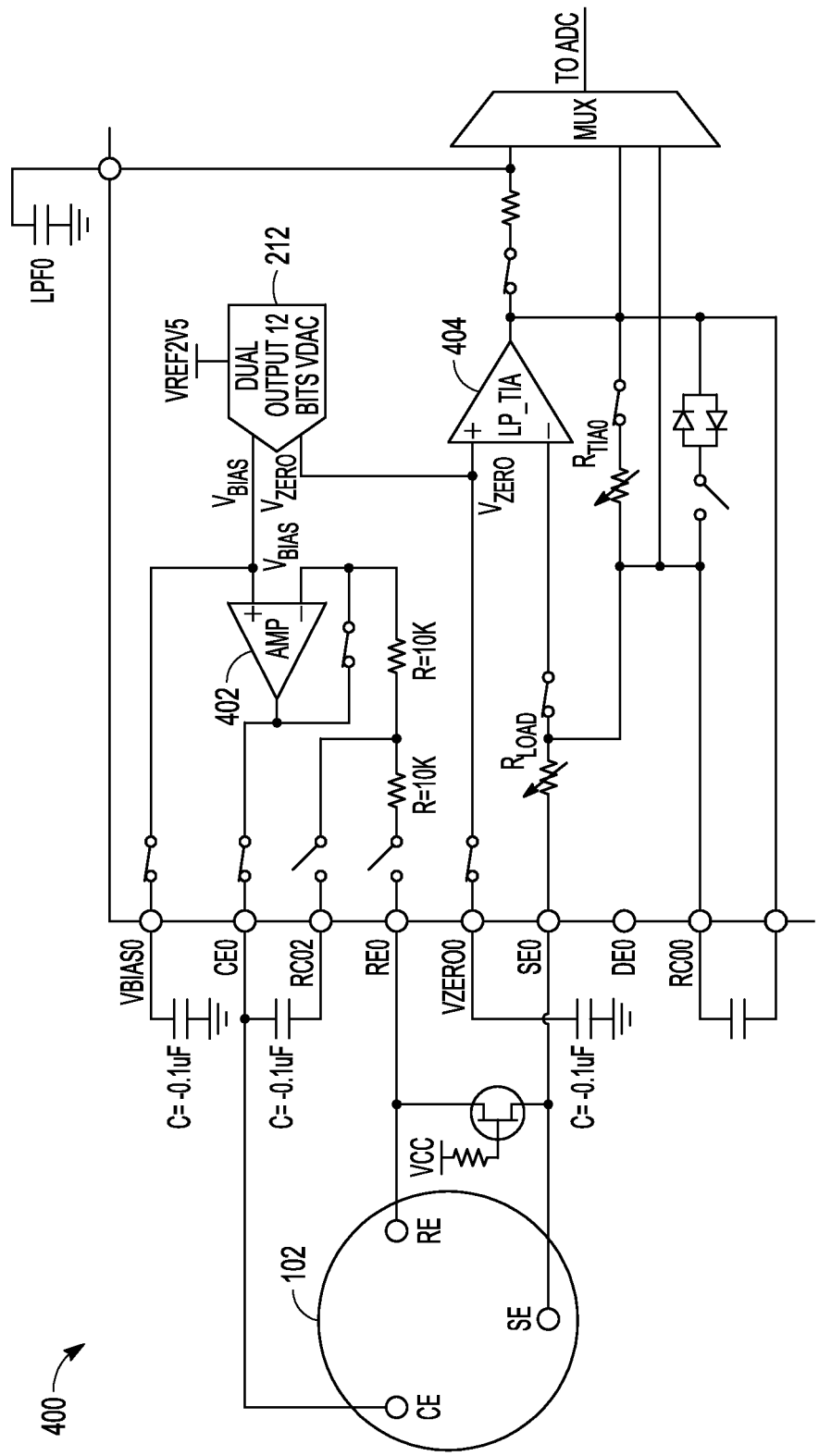
FIG. 4 shows an example of portions of a sensor interface circuit that can be used to provide a potentiostat circuit during normal gas-sensing operation of the sensor.

FIG. 4 shows an example of portions of a sensor interface circuit 400, such as can be integrated on the same monolithic integrated circuit (IC) chip as either of the sensor characteristic interface circuit 100 or the sensor characteristic interface circuit 200. The sensor interface circuit 400 can be used to provide a potentiostat circuit during normal gas-sensing operation of the sensor 102. Since the normal low-frequency response gas-sensing operation of the sensor 102 can be used almost full-time, seldom interrupted and then generally only briefly to perform the higher frequency sensor condition characteristic test (e.g., impedance testing) to determine sensor condition or usability, the sensor interface circuit 400 can be implemented using at least some lower power consumption components than those used in the sensor characteristic interface circuits 100, 200, although some components (e.g., dual-output DAC 212) can optionally be shared between the sensor interface circuit 400 and the selected sensor characteristic interface circuit 100, 200.

In a three electrode example, the working electrode (WE) can respond to the target gas to be detected, such as by oxidizing or reducing the gas. This creates a current flow that is proportional to the concentration of the target gas. This current can be supplied to the sensor through the counter electrode (CE). The reference electrode (RE) can be used by the potentiostat circuit to maintain a fixed potential at the working electrode, which can be maintained at the same potential as the reference electrode potential (e.g., for an unbiased sensor 102) or with an offset voltage (e.g., for a sensor 102 that requires a biasing). The counter electrode CE completes the circuit with the working electrode WE. The counter electrode CE will perform a reduction of a chemical constituent when the working electrode WE is oxidizing. The counter electrode CE will perform an oxidation of a chemical constituent when the working electrode WE is performing a reduction. The potential of the counter electrode CE can be allowed to float, such as to change in response to the concentration of the target. The potential on the counter electrode CE can be regarded as unimportant, so long as the potentiostat circuit can provide enough voltage and current to maintain the working electrode WE at the same potential as the reference electrode RE.

In the example of FIG. 4 a first output of the dual output DAC 212 can be used to establish the potential at Vzero provided to the working electrode WE (also referred to as the sensing electrode SE). A second output of the dual output DAC 212 can be used to establish the potential at the counter electrode CE and the non-inverting input of amplifier 402, which can be switchably-configured into a voltage-follower configuration to drive the counter electrode CE. The amplifier 402 supplies current to the counter electrode CE to balance the current required by the working electrode WE, SE. The inverting input of the amplifier 402 can be coupled to the reference electrode RE, such as through one or more resistors, such as the two series-connected 10 KΩ resistors shown in FIG. 4. The current through the working electrode WE, SE indicates concentration of the target gas, and can be converted into a resulting output voltage signal via a low power transimpedance amplifier 404, to which it can be coupled, such as through a load resistor Rload0. The gain of the transimpedance amplifier 404 can depend on the resistance value of Rload0 and a resistance value of a feedback resistor RTIA0 between an output of the transimpedance amplifier 404 and an inverting input of the transimpedance amplifier 404. The non-inverting input of the transimpedance amplifier 404 can be biased at a desired bias voltage, such as the voltage at Vzero provided by the second output of the dual-output DAC 212, at which the working electrode WE, SE is biased. The resistance values Rload0 and RTIA0 can be specified, compensated, or calibrated, for example, such as described in a U.S. Patent Application, filed on May 4, 2017, entitled INTERNAL INTEGRATED CIRCUIT RESISTANCE CALIBRATION (U.S. patent application Ser. No. 15/586,877), naming GuangYang Qu, Leicheng Chen, and Michael Looney as inventors, the disclosure of which is hereby incorporated herein by reference, in its entirety, including its disclosure of resistance measurement or calibration. The signal voltage output by transimpedance amplifier 404 can be provided (e.g., through an analog signal multiplexer circuit) to an analog-to-digital converter (ADC) circuit, for conversion to a digital signal. Further signal processing can be performed digitally, such as by a digital-signal processor (DSP) circuit.

Various Notes

The above description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round," a component that is not precisely circular (e.g., one that is slightly oblong or is a many-sided polygon) is still encompassed by this description.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. An impedance characteristic sensor interface circuit for independently delivering a differential stable bias signal component and a differential time-varying AC excitation signal component for testing an impedance of an electrochemical sensor having a sensor input node, first and second differential sensor feedback nodes, and a sensor output node, the sensor interface circuit including:
   an impedance excitation amplifier circuit, including:
      a first differential pair of inputs, coupled to receive the differential time-varying AC excitation signal component for communication onto first and second amplifier input nodes during a sensor impedance testing mode;
      a second differential pair of inputs, coupled to receive the differential stable bias signal component for communication onto the first and second amplifier input nodes; and
      a third differential pair of inputs, coupled to receive a feedback signal from the differential sensor feedback nodes for communication onto the first and second amplifier inputs nodes; and
   a sensor response amplifier circuit, coupled to the sensor for receiving a response signal to the differential time-varying AC excitation signal component, during the sensor impedance testing mode, for communication to a sensor response signal output node.

2. The sensor interface circuit of claim 1, comprising a first digital-to-analog converter (DAC) circuit, to convert a first digital input signal into a first analog signal for providing the differential time-varying AC excitation signal component.

3. The sensor interface circuit of claim 2, comprising a second DAC circuit, to convert a second digital input signal into a second analog signal for providing the differential stable bias signal component.

4. The sensor interface circuit of claim 3, wherein the second DAC circuit is also used to provide the differential stable bias signal component during an operating mode of the sensor during which the differential time-varying AC excitation signal component is not applied.

5. The sensor interface circuit of claim 3 wherein the second DAC circuit includes outputs to which shunt capacitors are respectively coupled.

6. The sensor interface circuit of claim 2, comprising an attenuating amplifier circuit to attenuate an output signal of the first DAC for providing the differential time-varying AC excitation signal component onto the first and second amplifier input nodes.

7. The sensor interface circuit of claim 1, comprising a load resistor to couple the sensor to at least one of (1) a transimpedance amplifier input of the sensor response amplifier circuit or (2) at least one of the differential sensor feedback nodes.

8. The sensor interface circuit of claim 1, wherein the differential time-varying AC excitation signal component is frequency-varying during the sensor impedance testing mode.

9. The sensor interface circuit of claim 1, wherein the differential stable bias signal component is temperature compensated.

10. A method of determining usability of an electrochemical sensor by determining an impedance associated with the electrochemical sensor, the method including:
   delivering a differential time-varying AC excitation signal component to first and second amplifier input nodes for driving an excitation signal into the sensor during a sensor impedance test;
   separately delivering a differential stable bias signal component to the first and second amplifier input nodes for biasing the first and second amplifier input nodes while driving the excitation signal into the sensor during the sensor impedance test;
   communicating a differential feedback signal from the sensor to the first and second amplifier input nodes while driving the excitation signal into the sensor; and
   measuring a response from the sensor while driving the excitation signal into the sensor during the sensor impedance test.

11. The method of claim 10, comprising:
   converting a first digital input signal into a first analog signal for providing the differential time-varying AC excitation signal component during the sensor impedance test; and
   converting a second digital input signal into a second analog signal for providing the differential stable bias signal component during the sensor impedance test.

12. The method of claim 11, further comprising also using the second analog signal for providing the differential stable bias signal component during an operating mode of the sensor during which the differential time-varying AC signal component is not applied.

13. The method of claim 11, comprising attenuating the first analog signal for providing the differential time-varying AC excitation signal component during the sensor impedance test.

14. The method of claim 11, comprising converting a current from the sensor in response to the differential time-varying AC excitation signal component into a voltage to provide an indication of a sensor characteristic related to usability of the sensor.

15. The method of claim 11, comprising varying a frequency of the differential time-varying AC signal component during the sensor impedance test.

16. The method of claim 11, comprising temperature compensating the differential stable bias signal component.

17. The method of claim 11, comprising providing at least one of a proportional-to-absolute-temperature (PTAT) or complementary-to-absolute-temperature (CTAT) signal to generate the differential stable bias signal component.

18. An impedance characteristic sensor interface circuit for independently delivering a differential stable bias signal component and a differential time-varying AC excitation signal component for testing an impedance of an electrochemical sensor, the sensor interface circuit including:
an impedance excitation amplifier circuit, including:
a first digital-to-analog converter (DAC) circuit, to convert a first digital input signal into a first analog signal for providing the differential time-varying AC excitation signal component during a sensor impedance testing mode;
a second DAC circuit, to convert a second digital input signal into a second analog signal for providing the differential stable bias signal component during the sensor impedance testing mode; and
a sensor response amplifier circuit, coupled to the sensor for receiving a response signal to the differential time-varying AC excitation signal component, during the sensor impedance testing mode.

19. The sensor interface circuit of claim 18, comprising:
a first differential pair of inputs, coupled to receive the differential time-varying AC excitation signal component for communication onto first and second amplifier input nodes during a sensor impedance testing mode;
a second differential pair of inputs, coupled to receive the differential stable bias signal component for communication onto the first and second amplifier input nodes; and
a third differential pair of inputs, coupled to receive a feedback signal from the differential sensor feedback nodes for communication onto the first and second amplifier inputs nodes.

20. The sensor interface circuit of claim 19, in combination with an electrochemical sensor including a reference electrode, a working or sensing electrode, and a counter or auxiliary electrode, wherein:
the counter or auxiliary electrode is coupled to the sensor interface circuit to receive the differential time-varying AC excitation signal component superimposed on the differential stable bias signal component during the sensor impedance testing mode;
the reference electrode is coupled to one of the differential sensor feedback nodes of the sensor interface circuit; and
the sensing electrode is coupled to the other of the differential sensor feedback nodes of the sensor interface circuit and to the sensor response amplifier circuit.

21. The sensor interface circuit of claim 18, wherein the same second DAC circuit is configured to convert the second digital input signal into the second analog signal for providing the differential stable bias signal component during a gas sensing operating mode of the sensor during which the differential time-varying AC excitation signal component is not applied.

* * * * *